United States Patent
Suzuki et al.

(10) Patent No.: US 9,632,100 B2
(45) Date of Patent: Apr. 25, 2017

(54) SAMPLE PRETREATMENT SYSTEM THAT SUPPORTS MULTISYSTEM CONFIGURATION

(71) Applicant: HITACHI HIGH-TECHNOLOGIES CORPORATION, Tokyo (JP)

(72) Inventors: Iwao Suzuki, Tokyo (JP); Tadao Shimizu, Tokyo (JP); Shigeru Yano, Tokyo (JP); Koji Kamoshida, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 298 days.

(21) Appl. No.: 14/364,237

(22) PCT Filed: Dec. 18, 2012

(86) PCT No.: PCT/JP2012/082838
§ 371 (c)(1),
(2) Date: Jun. 10, 2014

(87) PCT Pub. No.: WO2013/099711
PCT Pub. Date: Jul. 4, 2013

(65) Prior Publication Data
US 2014/0373642 A1    Dec. 25, 2014

(30) Foreign Application Priority Data
Dec. 28, 2011  (JP) .................. 2011-287256

(51) Int. Cl.
*G01N 1/22* (2006.01)
*G01N 35/00* (2006.01)
(Continued)

(52) U.S. Cl.
CPC . *G01N 35/00732* (2013.01); *A61B 5/150755* (2013.01); *A61B 10/007* (2013.01);
(Continued)

(58) Field of Classification Search
USPC ...................................... 73/863.01
See application file for complete search history.

(56) References Cited

U.S. PATENT DOCUMENTS

| | | | |
|---|---|---|---|
| 5,985,215 A | 11/1999 | Sakazume et al. | |
| 6,599,476 B1 * | 7/2003 | Watson .............. | B65G 47/1471 141/1 |

(Continued)

FOREIGN PATENT DOCUMENTS

| | | | | |
|---|---|---|---|---|
| CN | WO 2008043303 A1 * | 4/2008 | ............. | G01N 35/02 |
| JP | 08-271530 A | 10/1996 | | |

(Continued)

OTHER PUBLICATIONS

International Preliminary Report on Patentability received in International Application No. PCT/JP2012/082838 dated Jul. 10, 2014.
(Continued)

*Primary Examiner* — Eric S McCall
*Assistant Examiner* — Mohammed E Keramet-Amircolai
(74) *Attorney, Agent, or Firm* — Mattingly & Malur, PC

(57) ABSTRACT

A host system recognizes a sample pretreatment system at which a primary sample has first arrived and records the information, if multiple containers containing the primary sample are input. Upon issuing an analysis request to the sample pretreatment system, the host system determines whether the primary sample (sample bearing the same barcode for sample identification) is input to a system different from the system to which the sample was input for the first time and, if that is the case, then determines that "the sample is input to the wrong system" and issues a "do-nothing request" (request to do nothing) so that an aliquoting operation will not be performed. Given the "do-nothing request" from the host system, the sample pretreatment (Continued)

system does not prepare any aliquot sample and places the input sample onto a tray in a predetermined position.

8 Claims, 9 Drawing Sheets

(51) Int. Cl.
    *G01N 35/02*     (2006.01)
    *A61B 5/15*     (2006.01)
    *A61B 10/00*     (2006.01)

(52) U.S. Cl.
    CPC ....... *G01N 35/00871* (2013.01); *G01N 35/02* (2013.01); *G01N 2035/00752* (2013.01); *G01N 2035/00831* (2013.01); *G01N 2035/00891* (2013.01)

(56) References Cited

U.S. PATENT DOCUMENTS

| | | | | |
|---|---|---|---|---|
| 7,700,043 | B2* | 4/2010 | Mimura | G01N 35/00663 422/65 |
| 8,839,944 | B2* | 9/2014 | Takai | G01N 35/026 198/346.1 |
| 2007/0027635 | A1 | 2/2007 | Yamasaki et al. | |
| 2008/0047369 | A1* | 2/2008 | Tsujimura | G01N 35/00732 73/863.01 |
| 2008/0240983 | A1 | 10/2008 | Harris | |
| 2008/0247914 | A1* | 10/2008 | Edens | G01N 35/0099 422/400 |
| 2011/0290040 | A1* | 12/2011 | Tatsutani | G01N 35/04 73/863.01 |
| 2012/0036944 | A1* | 2/2012 | Chida | G01N 35/00613 73/863.01 |
| 2012/0216632 | A1* | 8/2012 | Seki | G01N 30/20 73/863.01 |
| 2013/0061693 | A1 | 3/2013 | Sasaki et al. | |

FOREIGN PATENT DOCUMENTS

| | | |
|---|---|---|
| JP | 11-304812 A | 11/1999 |
| JP | 2000-088861 A | 3/2000 |
| JP | 2001-091519 A | 4/2001 |
| JP | 2001-159635 A | 6/2001 |
| JP | 2003-083991 A | 3/2003 |
| JP | 3425912 B2 | 5/2003 |
| JP | 2007-034604 A | 2/2007 |
| JP | 2007-040932 A | 2/2007 |
| JP | 2007-318819 A | 12/2007 |
| JP | 2010-156649 A | 7/2010 |
| JP | 2010-266271 A | 11/2010 |
| WO | 2011148897 A1 | 1/2011 |

OTHER PUBLICATIONS

Chinese Office Action received in corresponding Chinese Application No. 201280064661.X dated Mar. 12, 2015.
Extended European Search Report received in corresponding European Application No. 12861140.7 dated Jul. 23, 2015.

* cited by examiner

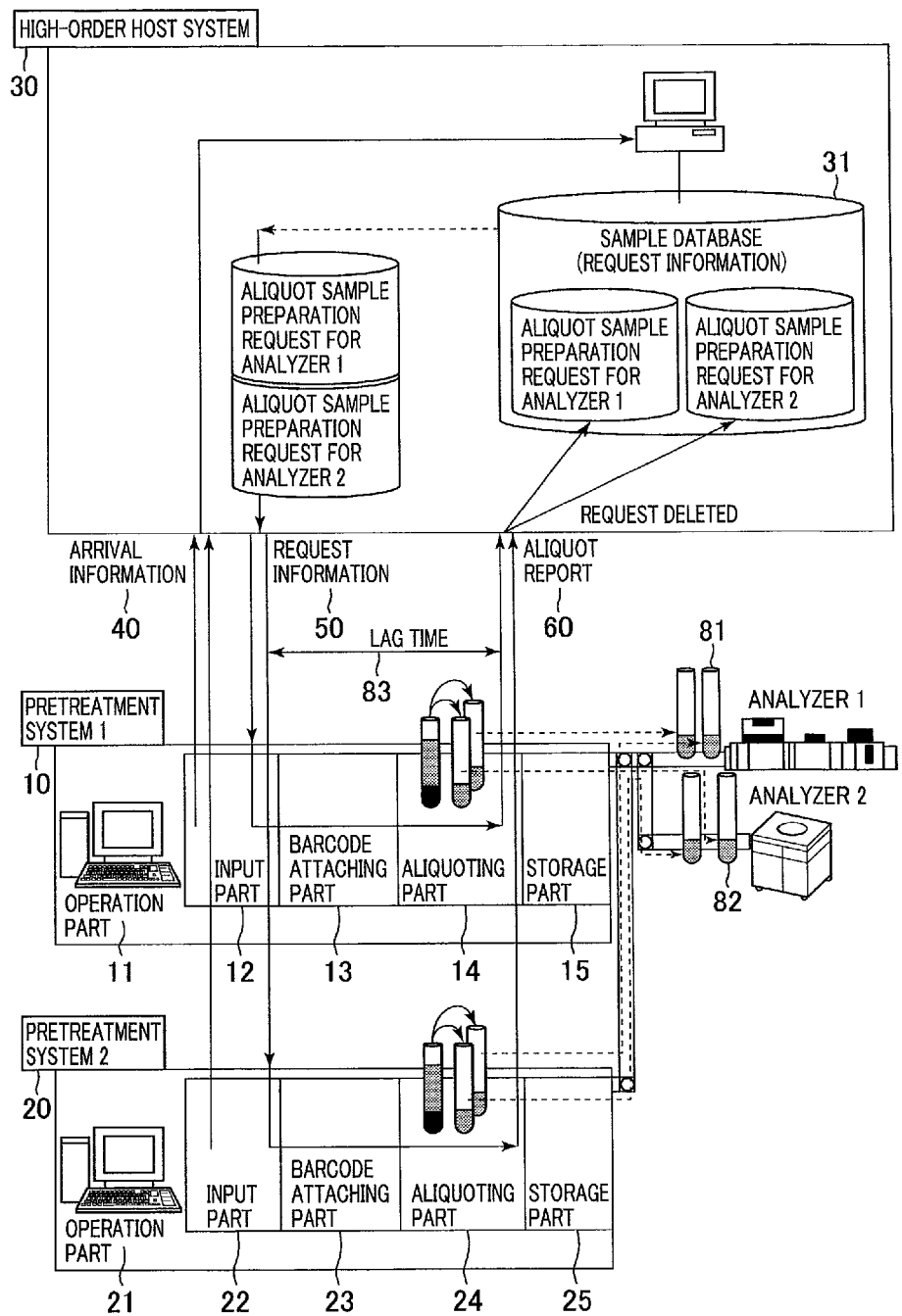

FIG. 5

| ALARM LIST | | | |
|---|---|---|---|
| NO. | MODULE NAME | LEVEL | MESSAGE |
| 123-123456 | IPB | CAUTION | INPUT TO WRONG SYSTEM |
| | | | |
| | | | |
| | | | |

| EXPLANATION AND COUNTERMEASURES | |
|---|---|
| NO. | 123-123456 |
| LEVEL | CAUTION |
| EXPLANATION | THE SAMPLE IS INPUT TO THE WRONG SYSTEM. |
| COUNTERMEASURES | THE SAMPLE IN A SECOND OR SUBSEQUENT CONTAINER IS INPUT PRESUMABLY TO THE WRONG SYSTEM. VERIFY THE SAMPLE, AND INPUT THE SAMPLE AGAIN TO THE SYSTEM TO WHICH THE SAMPLE WAS INPUT FOR THE FIRST TIME. |

SAMPLE PRETREATMENT SYSTEM THAT SUPPORTS MULTISYSTEM CONFIGURATION

TECHNICAL FIELD

The present invention relates to techniques for smoothly operating a multisystem configuration formed by sample pretreatment systems for clinical examination.

BACKGROUND ART

In the field of clinical examination, it has been desired in recent years to raise the speed of treatment by sample pretreatment systems that perform pretreatment such as aliquoting on samples including blood and urine for biochemical analyses or immunoassays. One way of boosting the efficiency of such treatment is by configuring a plurality of sample pretreatment systems for treating numerous samples in parallel.

In that system configuration, it might happen that a sample bearing the same barcode is input a number of times or that the sample in multiple containers bearing the same barcode is input. In such cases, aliquot samples that have already been prepared could be prepared again unnecessarily.

For example, there may be the case where a sample, once input and finished in treatment, needs to be again treated for re-examination or for other reasons, or the case where a sample of a large volume is input in multiple sample containers. In these cases, the sample bearing the same barcode needs to be input a number of times (or introduced in multiple containers) to the system. In a system configuration that involves only one sample pretreatment system, the sample in containers bearing the same barcode is input to the same system. Thus the system can determine whether these samples are "input for the first time" or "input a second or subsequent time." Meanwhile, in a system configuration in which multiple sample pretreatment systems are connected, if the sample in multiple containers bearing the same barcode is input to different sample pretreatment systems, it is impossible for each system to determine whether the sample it is given is "input for the first time" or "input a second or subsequent time."

In an example such as one shown in FIG. 3 where a plurality of sample pretreatment systems are connected to form a multisystem configuration and where a primary sample in multiple containers (each bearing the same barcode for sample identification) is input, the primary sample in a first container may be input to one sample pretreatment system and the primary sample in a second or subsequent container may be input to another sample pretreatment system. In this case, each sample pretreatment system determines that the input primary sample is "input for the first time" and prepares aliquot samples to be used to perform analysis for the all analysis items that the primary sample is requested. Thus multiple aliquot samples (81, 82) are prepared for the same analysis item, which leads to the output of multiple measurements of the same item.

In view of the above problem, processes may be performed conceivably to delete aliquot sample preparation request information from within a host system upon transmission of an aliquot report (60) thereto so that no further aliquot sample will be prepared in duplicate regarding the analysis item for which aliquoting has been finished. However, between the time when the host system transmits aliquot sample preparation request information to one sample pretreatment system and the time when an aliquot report is sent back from the same system, the sample in a second or subsequent container could be input to another sample pretreatment system. In that case, the request information cannot be deleted in time because of a time lag (83), and the same problem mentioned above cannot be avoided.

This has led to other problems such as the drop in the treatment efficiency of the entire system attributable to the preparation of unnecessary aliquot sample, and rising running costs due to the excess use of consumables such as aliquot sample containers.

Thus in the case of a system configuration having multiple sample pretreatment systems connected therein, it has been necessary to take measures not to input the sample bearing the same barcode a number of times (or in multiple containers), such as limitations on system use by customers. The system configuration including a plurality of sample pretreatment systems is disclosed in Patent Literature 1, for example. The method of carrying out processes upon input of a primary sample in multiple containers is disclosed in Patent Literature 2.

PRIOR ART LITERATURE

Patent Literature

Patent Literature 1
  JP-2001-159635-A
Patent Literature 2
  JP-2007-040932-A

SUMMARY OF THE INVENTION

Problem to be Solved by the Invention

In view of the above problem and according to the present invention, there is provided a sample pretreatment system configured to accommodate multiple sample pretreatment system whereby aliquot samples are not prepared in duplicate if the same primary sample is input a number of times or introduced in multiple containers.

Means for Solving the Problem

In order to solve the above problem, a control method used in a system according to the present invention works as shown in FIG. 1. When a sample is input to a sample pretreatment system and confirmation of the sample arrival is transmitted to a host system, if multiple containers containing the primary sample are input, the host system recognizes the sample pretreatment system at which the primary sample has first arrived and records the information. Later, when issuing an analysis request to the sample pretreatment system, the host system determines whether the primary sample (i.e., sample bearing the same barcode for sample identification) is input to a system different from the system to which the sample was input for the first time. If the systems are found different, then the host system determines that "the sample is input to the wrong system" and issues a do-nothing request (i.e., request to do nothing) so that an aliquoting operation will not be performed. Given the do-nothing request from the host system, the sample pretreatment system does not prepare any aliquot sample and places the input sample onto a tray in a predetermined position. At the moment the sample is placed onto the tray, the sample pretreatment system presents the customer with an alarm indicating that "the sample is input to the wrong system."

As a similar measure, a shared database connected to a shared communication line interconnecting multiple systems may be used in place of the host system as a medium for recognizing the sample pretreatment system at which the primary sample has first arrived and recording the information, as shown in FIG. 2.

Effect of the Invention

According to the present invention, where a multisystem configuration is provided including multiple sample pretreatment systems and where a primary sample is present in multiple containers, even if a customer inadvertently inputs the primary sample contained in another container into a system different from the one to which the primary sample was first input, there does not occur the problem in which an aliquot sample regarding an item for which aliquoting has been reported is prepared again. Further, an alarm display prompts the customer to input the sample again to the correct system.

BRIEF DESCRIPTION OF THE DRAWINGS

FIG. 4 is an explanation drawing 2 of the problem with the multisystem configuration.
FIG. 5 shows a display example of an alarm display part.

MODE FOR CARRYING OUT THE INVENTION

Some embodiments of the present invention will now be described in detail with reference to the accompanying drawings.

First Embodiment

Figure 1:
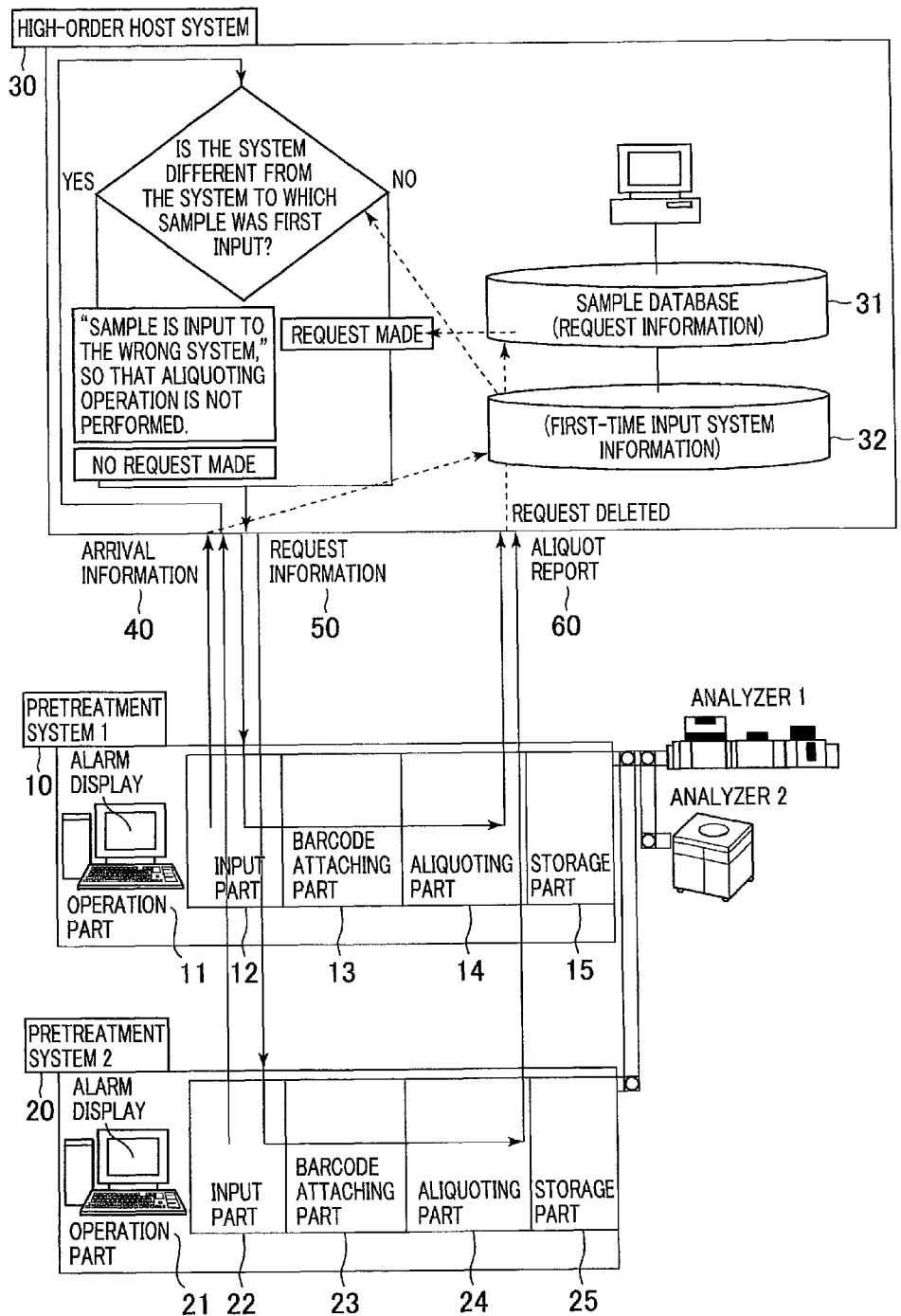
FIG. 1 shows a sample pretreatment system that supports a multisystem configuration.

FIG. 1 is a block diagram showing a sample pretreatment system that supports a multisystem configuration according to the present invention.
In FIG. 1, a sample pretreatment system 1(10) and another sample pretreatment system 2(20) each constitute a system that prepares an aliquot sample from an input primary sample for analysis with an analyzer (1, 2). Each system is made up of an operation part (11, 21) having an alarm display function, a barcode attaching part (13, 23), an aliquoting part (14, 24), and a storage part (15, 25). The sample pretreatment systems 1 and 2 (10, 20) can communicate with a host system via communication lines.
When a primary sample arrives at an input part of the sample pretreatment system, a barcode attached to the primary sample container is read and information about the primary sample is thereby obtained. The acquired primary sample information is transmitted from the sample pretreatment system to the host system as primary sample arrival information (40). Incidentally, the storage medium on which primary sample information is stored is not limited to the barcode label; an RFID may be used instead for example. The host system references a sample database (of first-time input information) (32) to determine whether the primary sample information is already recorded in the first-time input system information. If the primary sample information is found in the first-time input system information, the host system determines that the primary sample in question is input a second or subsequent time or introduced in a second or subsequent container. If the primary sample information is not found in the sample database of the host system (first-time input system information), the host system determines that the primary sample about which the information has been transmitted is input for the first time, and records to the first-time input system information the primary sample information and the information identifying the sample pretreatment system that has transmitted the primary sample arrival information.

If the sample is determined to be input a second or subsequent time or introduced in a second or subsequent container, the host system determines whether the sample pretreatment system that has transmitted the primary sample arrival information (40) is the same as the sample pretreatment system to which the sample was input for the first time and which is recorded in the first-time input system information (32). If the sample is determined to be input to the same sample pretreatment system as before, the host system references a sample database (request information) (31) and thereby sends aliquot sample preparation request information (50) back to the sample pretreatment system that has transmitted the primary sample arrival information (40). Based on the request information (50), the sample pretreatment system causes its aliquoting part to perform an aliquoting operation. Upon completion of the aliquoting operation, the sample pretreatment system transmits an aliquot report (60) to the host system. The aliquot sample prepared by the aliquoting operation is transported to the analyzer 1 or 2.

On the other hand, if it is determined that the sample is input a second or subsequent time or in a second or subsequent container and that the sample pretreatment system that has transmitted the primary sample arrival information (40) is different from the sample pretreatment system that is recorded in the first-time input system information (32), the host system determines that "the sample is input to the wrong system" and transmits the request information (50) of "do-nothing request (request to do nothing)" to the sample pretreatment system in question so as not to perform an aliquoting operation. Given the do-nothing request, the sample pretreatment system does not perform an aliquoting operation, displays an alarm such as one shown in FIG. 5, and does not prepare aliquot samples in duplicate.

Figure 6:
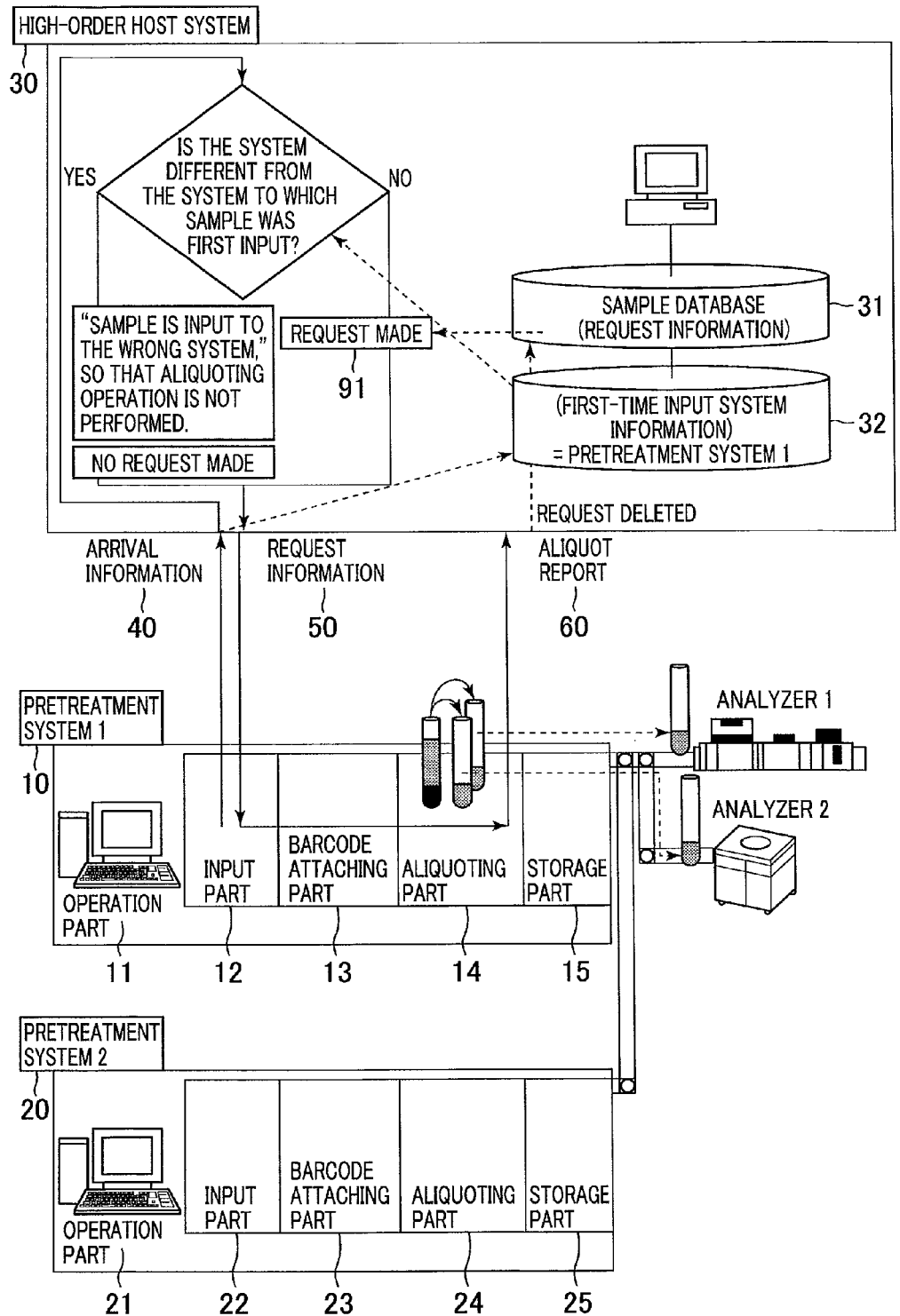
FIG. 6 shows a processing flow of a first embodiment (at normal time).

FIG. 6 shows a processing flow in the case where the first-time input system information indicates the sample pretreatment system 1(10) and where the sample in a second or subsequent container is also input to the same sample pretreatment system 1(10).

Upon detecting that the primary sample is input to an input part (12), the sample pretreatment system 1(10) transmits the primary sample arrival information (40) to the host system (30). Based on the primary sample information thus transmitted, the host system (30) references the first-time input system information (32).

In the first-time input system information (32), the sample pretreatment system 1(10) is recorded as the system to which the sample was input for the first time for treatment, and the system 1(10) coincides with the system to which the sample is input this time. Thus the host system (30) determines that a "request is made" (91) and transmits the aliquot sample preparation request information (50) recorded in the sample database (request information) (31) to the sample pretreatment system. Given the request information (50), the sample pretreatment system performs an aliquoting operation. Upon completion of the aliquoting operation, the sample pretreatment system transmits an aliquot report (60) to the host system. The aliquot sample prepared by the aliquoting operation is transported to the analyzer 1 or 2.

Figure 7:
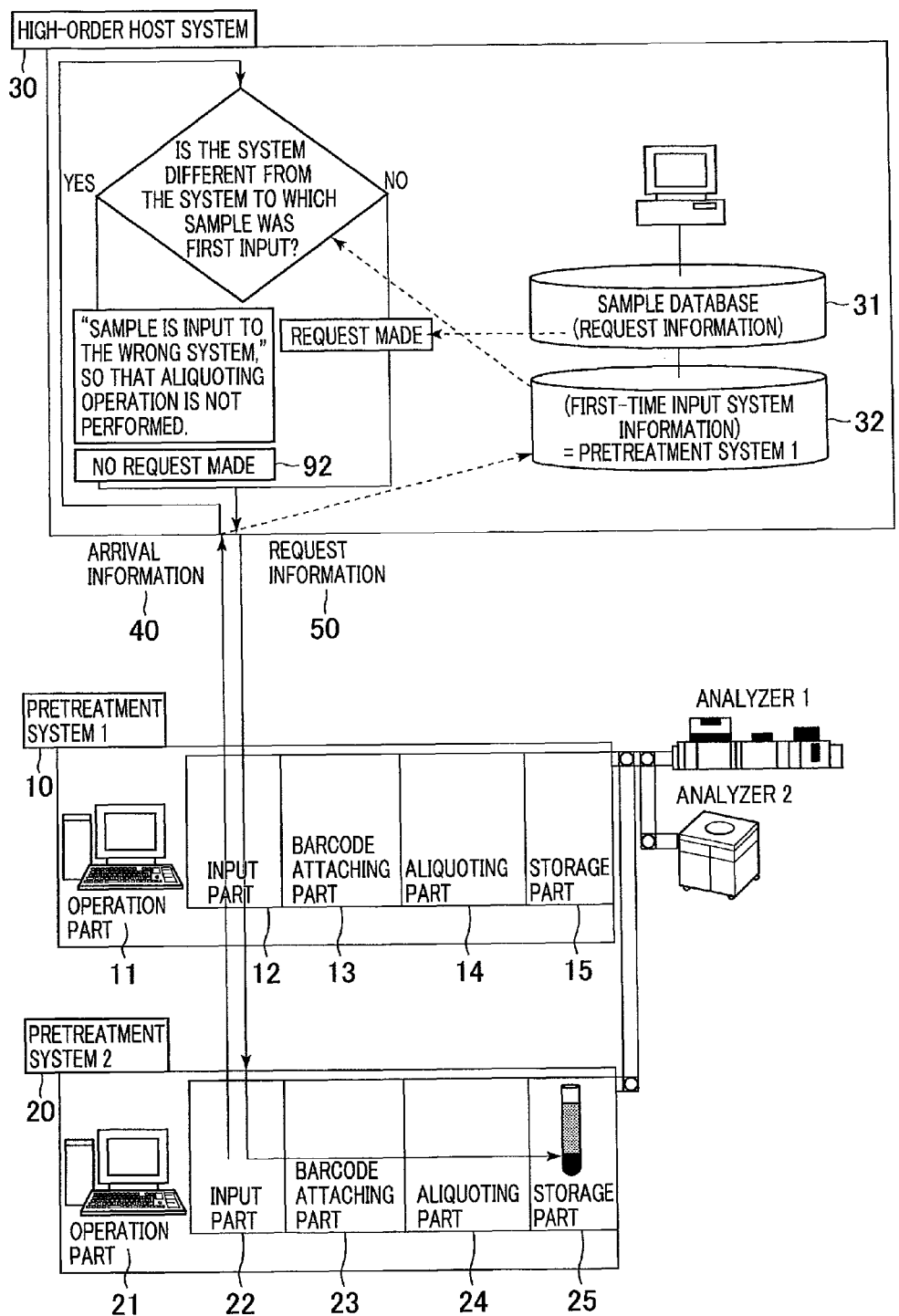
FIG. 7 shows a processing flow of the first embodiment (in effect when the sample is input to the wrong system).

FIG. 7 shows a processing flow in the case where the first-time input system information indicates the sample pretreatment system 1(10) and where the sample in a second or subsequent container is input to the sample pretreatment system 2(20).

Upon detecting that the primary sample is input to an input part (22), the sample pretreatment system 2(20) transmits the primary sample arrival information (40) to the host system (30). Based on the primary sample information thus transmitted, the host system (30) references the first-time input system information (32).

In the case of FIG. 7, the sample pretreatment system 1(10) is recorded in the first-time input system information as the system to which the sample was input for the first time for treatment, the system 1(10) being different from the system from which the primary sample arrival information (40) has been received this time. Thus the host system determines that "the sample is input to the wrong system" and transmits the request information (50) of "do-nothing request (request to do nothing) (92)" to the sample pretreatment system so as not to perform an aliquoting operation. Given the do-nothing request, the sample pretreatment system does not perform an aliquoting operation and displays an alarm such as one shown in FIG. 5. The primary sample is stored into the storage part (25).

Second Embodiment

Explained next is a system as another embodiment of the present invention that has a shared database.

Figure 2:
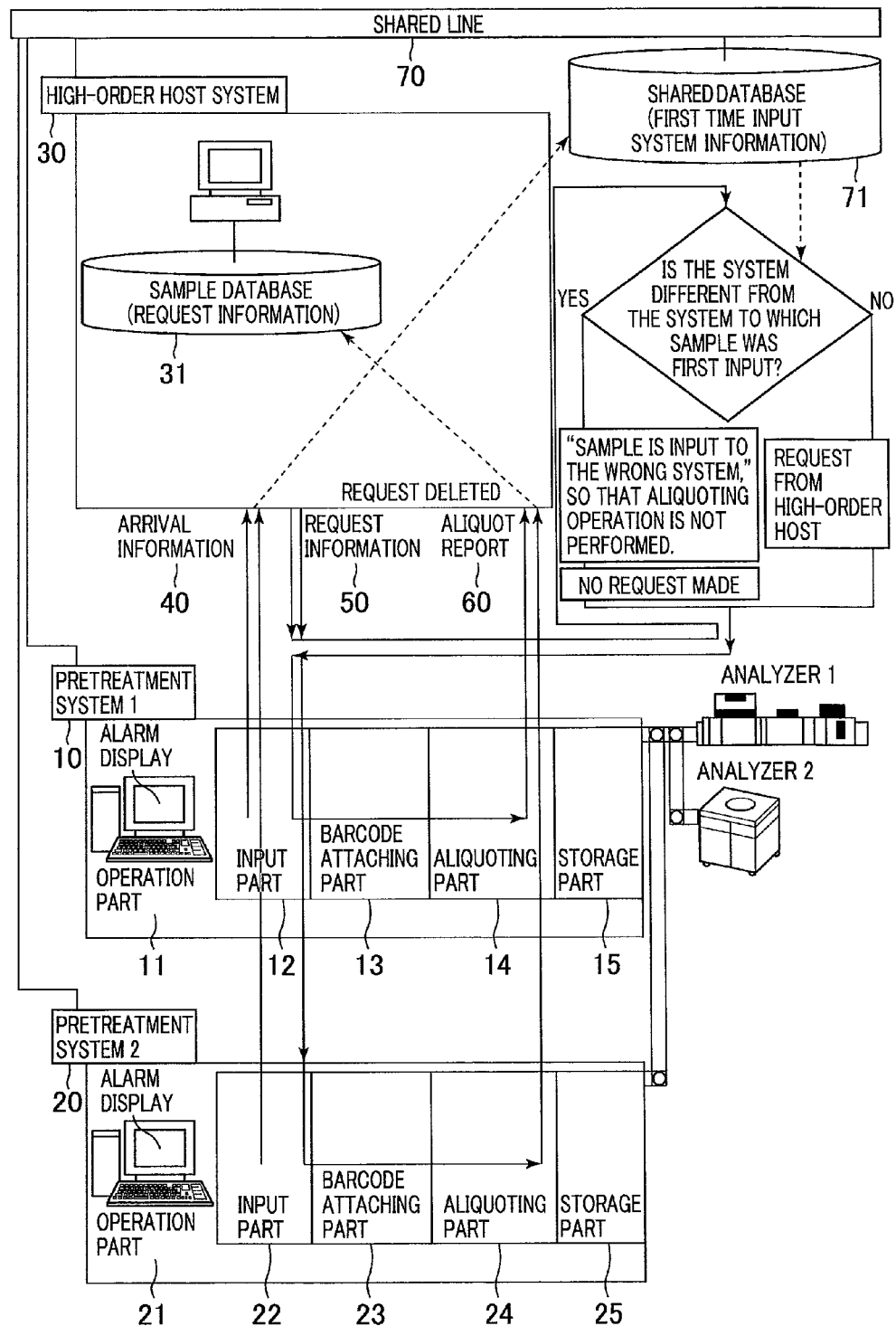
FIG. 2 shows a sample pretreatment system that supports a multisystem configuration utilizing a shared database.
Figure 3:
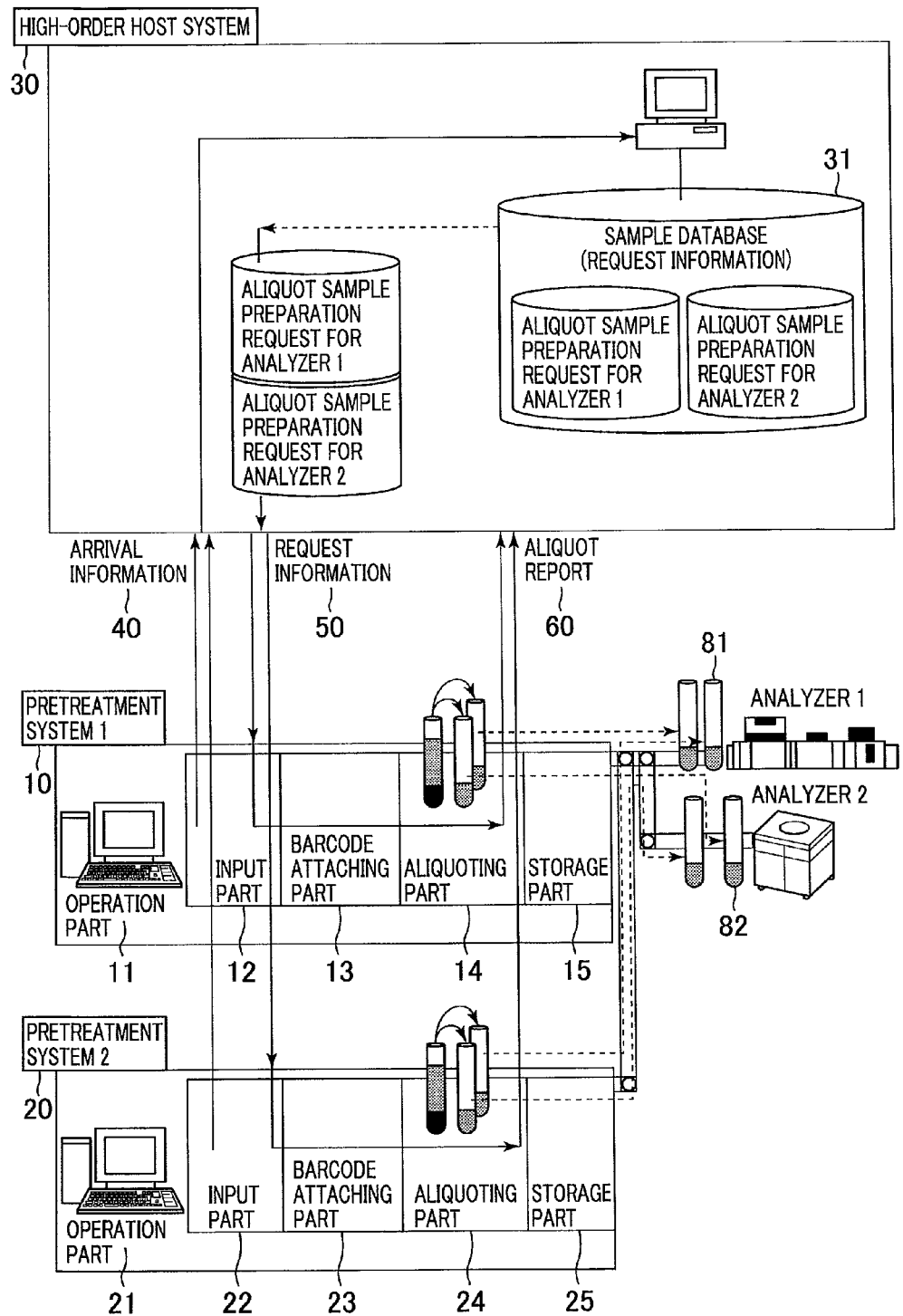
FIG. 3 is an explanation drawing 1 of the problem with the multisystem configuration.

FIG. 2 is a block diagram showing a sample pretreatment system that supports a multisystem configuration utilizing a shared database according to the present invention.

In FIG. 2, a sample pretreatment system 1(10) and another sample pretreatment system 2(20) are each made up of an operation part (11, 21) having an alarm display function, a barcode attaching part (13, 23), an aliquoting part (14, 24), and a storage part (15, 25). A host system, the sample pretreatment systems 1(10) and 2(20), and a shared database (first-time input system information)(71) are configured to be connected via a shared line (70).

When a new primary sample arrives at the sample pretreatment system, a barcode attached to the primary sample container is read and information about the primary sample is thereby obtained. The acquired primary sample information is transmitted from the sample pretreatment system to the host system as primary sample arrival information (40).

The host system references the sample database (request information) (31) using the primary sample information as the key, and sends aliquot sample preparation request information (50) back to the sample pretreatment system.

Concurrently, upon arrival of the primary sample, the sample pretreatment system queries the shared database (first-time input system information) (71) to determine whether the primary sample information is already stored in the shared database.

If the primary sample information in question is not found in the shared database, it is determined that this primary sample container is input for the first time, and the primary sample information and the information identifying the sample pretreatment system that has transmitted the primary sample arrival information are stored into the shared database.

If the primary sample information is found in the shared database, it is determined whether the sample pretreatment system to which the sample is input this time is the same as the sample pretreatment system to which the sample was input for the first time. If it is determined that the sample pretreatment system to which the sample is input this time is the same as the sample pretreatment system to which the sample was input for the first time, the sample pretreatment system performs an aliquoting operation based on the aliquot sample preparation request information (50). Upon completion of the aliquoting operation, an aliquot report (60) is transmitted to the host system. The aliquot sample prepared by the aliquoting operation is transported to the analyzer 1 or 2. If it is determined that the sample pretreatment system to which the sample is input this time is different from the sample pretreatment system to which the sample was input for the first time, the sample pretreatment system with the sample input thereto this time can query the shared database to recognize that the input system information (71) is different. Thus the sample pretreatment system does not perform the aliquoting operation, displays an alarm such as one shown in FIG. 5, and does not prepare aliquot samples in duplicate.

Figure 8:
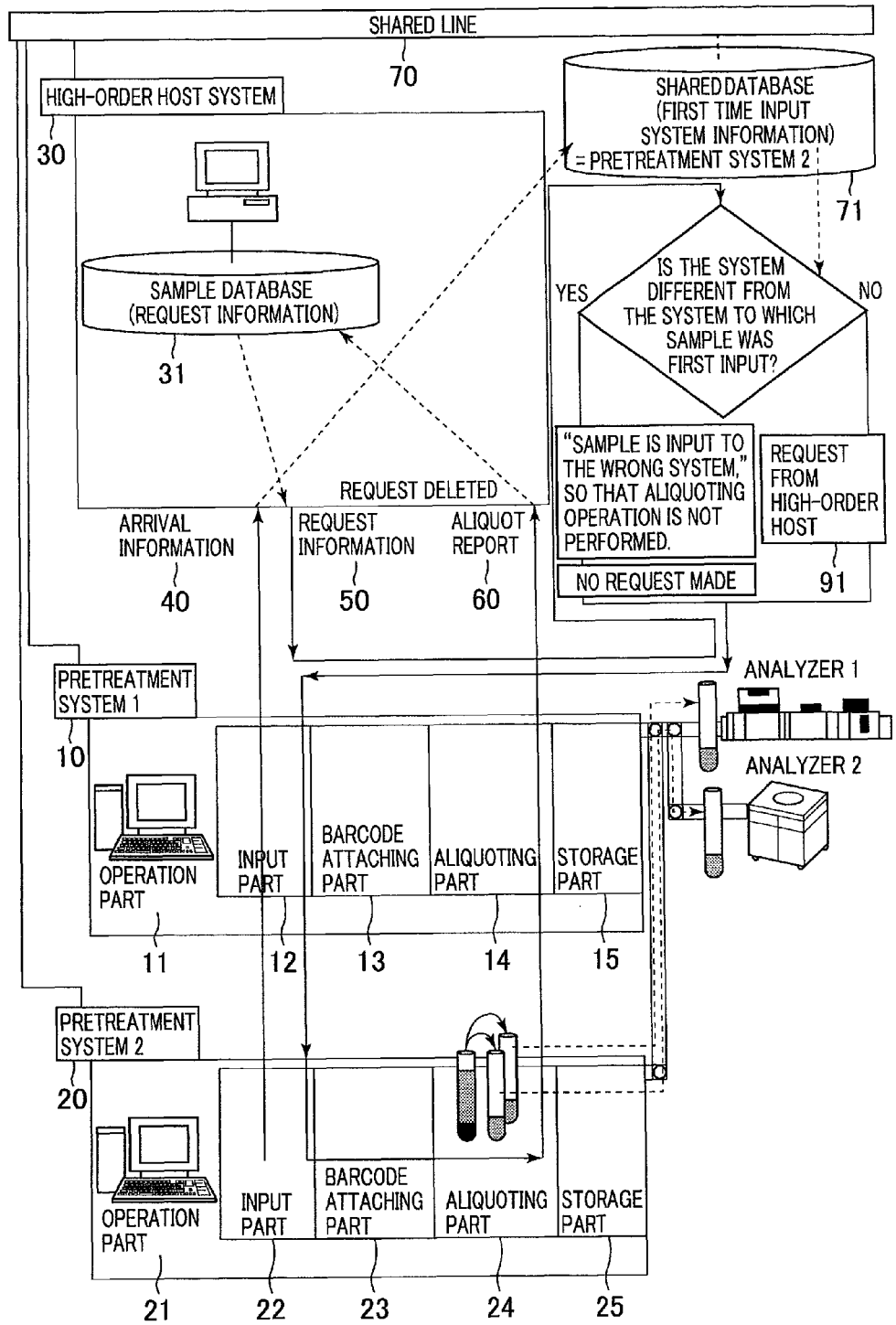
FIG. 8 shows a processing flow of a second embodiment (at normal time).

FIG. 8 shows a processing flow in the case where the first-time input system information indicates the sample pretreatment system 2(20) and where the sample in a second or subsequent container is also input to the sample pretreatment system 2(20).

Upon detecting that the primary sample is input to the input part (22), the sample pretreatment system 2(20) transmits the primary sample arrival information (40) to the host system (30). At the same time, the sample pretreatment system 2(20) references the first-time input system information (71) via the shared line 70.

In the first-time input system information, the sample pretreatment system 2(20) is recorded as the system to which the sample was input for the first time for treatment, the system 2(20) coinciding with the system to which the sample is input this time. Thus the sample pretreatment system selects "execution of the request from the host system (91)" and performs an aliquoting operation based on the request information (50) transmitted from the host system. Upon completion of the aliquoting operation, an aliquot report (60) to that effect is transmitted to the host system. The aliquot sample prepared by the aliquoting operation is transported to the analyzer 1 or 2.

Figure 9:
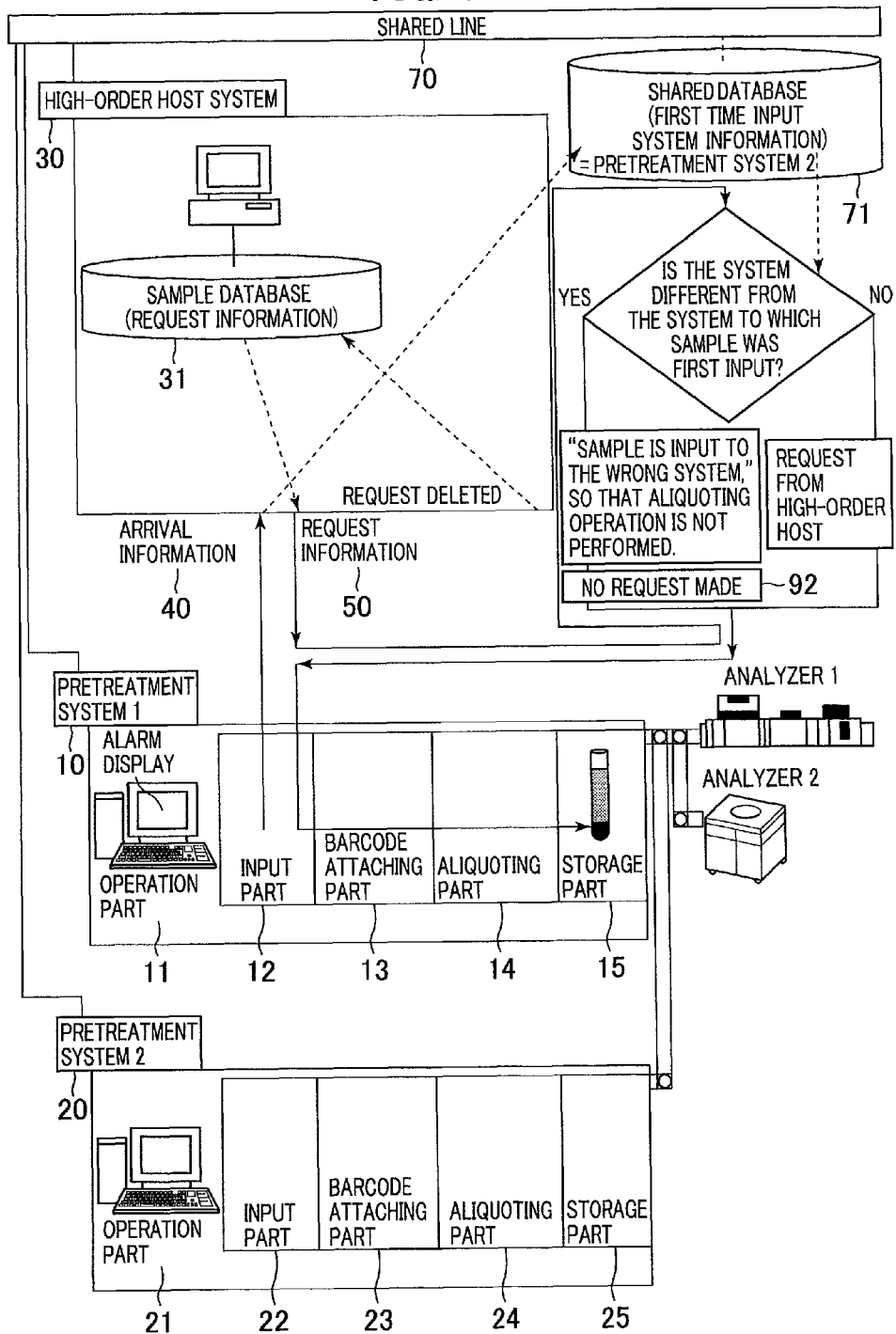
FIG. 9 shows a processing flow of the second embodiment (in effect when the sample is input to the wrong system).

FIG. 9 shows a processing flow in the case where the first-time input system information indicates the sample pretreatment system 2(20) and where the sample in a second or subsequent container is input to the sample pretreatment system 1(10).

Upon detecting that the primary sample is input to the input part (12), the sample pretreatment system 1(10) transmits the primary sample arrival information (40) to the host system (30). At the same time, the sample pretreatment system 1(10) references the first-time input system information (71) via the shared line 70.

In the first-time input system information, the sample pretreatment system 2(20) is recorded as the system to which the sample was input for the first time for treatment, the system 2(20) being different from the system to which the sample is input this time. Thus the sample pretreatment system determines that "the sample is input to the wrong system," selects "do-nothing request (92)," and ignores the aliquot sample preparation request information (50) transmitted from the host system so as not to perform an aliquoting operation. With no aliquoting operation performed, the primary sample is stored into the storage part (15) of the sample pretreatment system 1(10), and an alarm such as one shown in FIG. 5 is displayed.

Third Embodiment

A further embodiment of the present invention is explained below.

For example, consider the case where the aliquoting part prepares an aliquot sample from the sample that was input to the sample pretreatment system 1(10) for the first time for treatment and, with the primary sample stored into the storage part, the primary sample is again input to the sample pretreatment system because of a request to analyze another analysis item. When the aliquoting operation for the first-time treatment is finished, the sample pretreatment system 1(10) transmits an aliquot report to the host system (30). Upon receipt of the aliquot report, the host system references the sample information in the sample database to add a flag to the analysis item for which the aliquot sample has already been prepared or to delete the relevant request.

When the operator inputs the sample again to the sample pretreatment system 2(20), the sample pretreatment system 2(20) detects that the same sample is again input and transmits the primary sample arrival information (40) to the host system. Upon detecting the query made from the sample pretreatment system to which the same sample is again input, the host system references the request information about the sample in question and returns the aliquot sample preparation request information requesting the sample pretreatment system 1(10) to prepare an aliquot sample for an analysis item except for that with the flag indicating that the aliquot sample has already been prepared.

This embodiment requires that a sufficient time period elapse between the first-time treatment and a second or subsequent treatment, such as when a given sample, after being placed in storage, needs to be again treated. Still, this kind of treatment makes it possible unfailingly to prepare aliquot samples of the sample that is again input.

DESCRIPTION OF REFERENCE CHARACTERS

10 Sample pretreatment system 1
11 Operation part of sample pretreatment system 1
12 Input part of sample pretreatment system 1
13 Barcode attaching part of sample pretreatment system 1
14 Aliquoting part of sample pretreatment system 1
15 Storage part of sample pretreatment system 1
20 Sample pretreatment system 2
21 Operation part of sample pretreatment system 2
22 Input part of sample pretreatment system 2
23 Barcode attaching part of sample pretreatment system 2
24 Aliquoting part of sample pretreatment system 2
25 Storage part of sample pretreatment system 2
30 Host system
31 Sample database (request information) in host system
32 Sample database (first-time input system information) in host system
40 Primary sample arrival information transmitted from sample pretreatment system to host system
50 Request information transmitted from host system to sample pretreatment system
60 Aliquot report transmitted from sample pretreatment system to the host system
70 Shared line
71 Shared database (first-time input system information)
81 Multiple aliquot examples fed to analyzer 1
82 Multiple aliquot examples fed to analyzer 2
83 Time lag between request information and aliquot report
91 Processing in the case where aliquoting is performed as requested because the system is the same as the system of the first-time input
92 Processing in the case where aliquoting is not performed because the system is different from the system of the first-time input

The invention claimed is:

1. A control method used in a system including a plurality of sample pretreatment systems, the control method comprising:
   when a sample is input to a first sample pretreatment system of the sample pretreatment systems, determining whether a same sample was previously input to a second sample pretreatment system of the sample pretreatment systems;
   when the same sample was previously input to the second sample pretreatment system, recovering the sample from the first sample pretreatment system without aliquoting the sample in the first sample pretreatment system; and
   displaying an alarm that the same sample was previously input to the second sample pretreatment system,
   wherein the same sample is determined to have been previously input to the second sample pretreatment system when the second sample pretreatment system reads and transmits sample information of the same sample before the first sample pretreatment system reads and transmits sample information of the sample.

2. The control method according to claim 1, further comprising:
   when the same sample was not previously input to the second sample pretreatment system, aliquoting the same sample in the first sample pretreatment system.

3. The control method according to claim 1, further comprising:
   when the same sample was previously input to the second sample pretreatment system, aliquoting the same sample in the second sample pretreatment system.

4. The control method according to claim 2, wherein the same sample is input to the first sample pretreatment system and the second sample pretreatment system in different containers.

5. The control method according to claim 1, wherein the same sample from a second container in the second sample pretreatment system is aliquoted, and
   the sample in a first container in the first sample pretreatment system is recovered without aliquoting the sample from the first container.

6. A system for pretreating a plurality of sample containers, comprising:
   a host; and
   a plurality of sample pretreatment systems connected to the host, and each of the sample pretreatment systems includes:
   input means for receiving one or more of the sample containers,
   reading means for reading sample information from the sample containers received by the input means, and aliquoting means for aliquoting samples from the sample containers read by the reading means, wherein the host system is programmed to:

when a sample in a first sample container of the sample containers is input to a first sample pretreatment system of the sample pretreatment systems, determine whether a same sample in a second sample container of the sample containers was previously input to a second sample pretreatment system of the sample pretreatment systems, when the same sample in the second sample container was previously input to the second sample pretreatment system, recover the sample in the first sample container from the first sample pretreatment system without aliquoting the sample in the first sample container in the first sample pretreatment system; and display an alarm that the same sample in the second sample container was previously input to the second sample pretreatment system, wherein the same sample in the second sample container is determined to have been previously input to the second sample pretreatment system when the second sample pretreatment system is determined to have transmitted the sample information read from the second sample container by the reading means thereof to the host system before the first sample pretreatment system has transmitted the sample information read from the first sample container by the reading means thereof to the host system.

7. The system according to claim 6, wherein the host system is further programmed to:

when the same sample in the second sample container was not previously input to the second sample pretreatment system, instruct the first sample pretreatment system to aliquot the same sample in the first sample container in the first sample pretreatment system.

8. The sample pretreatment system according to claim 6, wherein the host system is further programmed to:

when the same sample was previously input to the second sample pretreatment system, instruct the second sample pretreatment system to aliquot the same sample in the second sample container.

\* \* \* \* \*